(12) United States Patent
Nargessi et al.

(10) Patent No.: US 7,264,927 B2
(45) Date of Patent: Sep. 4, 2007

(54) ISOLATION AND PURIFICATION OF NUCLEIC ACIDS

(75) Inventors: Ruhangiz D. Nargessi, Alameda, CA (US); Matt Pourfarzaneh, Alameda, CA (US)

(73) Assignee: Cortex Biochem, Inc., San Leandro, CA (US)

( * ) Notice: Subject to any disclaimer, the term of this patent is extended or adjusted under 35 U.S.C. 154(b) by 169 days.

(21) Appl. No.: 10/244,144

(22) Filed: Sep. 12, 2002

(65) Prior Publication Data

US 2003/0092045 A1 May 15, 2003

Related U.S. Application Data

(60) Provisional application No. 60/337,904, filed on Nov. 6, 2001.

(51) Int. Cl.
C12Q 1/68 (2006.01)
C07H 21/02 (2006.01)
C07H 21/04 (2006.01)
C07H 19/04 (2006.01)
G01N 1/18 (2006.01)

(52) U.S. Cl. .................. 435/6; 536/23.1; 536/24.3; 536/25.4; 536/25.41; 436/177; 436/178

(58) Field of Classification Search .............. 435/6; 536/23.1
See application file for complete search history.

(56) References Cited

U.S. PATENT DOCUMENTS

| | | | |
|---|---|---|---|
| 4,921,805 | A | 5/1990 | Gebeyehu et al. |
| 5,234,809 | A | 8/1993 | Boom et al. |
| 5,437,983 | A | 8/1995 | Watts et al. |
| 5,564,104 | A | 10/1996 | Pourfarzaneh |
| 5,705,628 | A | 1/1998 | Hawkins |
| 5,790,964 | A | 8/1998 | Pourfarzaneh |
| 5,804,684 | A | 9/1998 | Su |
| 5,898,071 | A | 4/1999 | Hawkins |
| 6,027,945 | A | 2/2000 | Smith et al. |
| 6,084,091 | A | 7/2000 | Muller et al. |
| 6,103,127 | A | 8/2000 | Pourfarzaneh |
| 6,416,671 | B1 | 7/2002 | Pourfarzaneh |

FOREIGN PATENT DOCUMENTS

| | | | |
|---|---|---|---|
| JP | 02-289598 | | 11/1990 |
| JP | 03-101689 | | 4/1991 |
| JP | 07-059572 | | 3/1995 |
| WO | WO86/05815 | | 10/1986 |
| WO | WO91/12079 | | 8/1991 |
| WO | WO96/09379 | | 3/1996 |
| WO | WO97/08547 | * | 3/1997 |
| WO | WO 01/62976 A1 | | 8/2001 |
| WO | WO 02/066993 | * | 8/2002 |
| WO | WO 03/033739 A1 | | 4/2003 |

OTHER PUBLICATIONS

Ausubel, F. M. et al., "Short Protocols in Molecular Biology", Third Edition, John Wiley & Sons, Inc., p. 9-52 (1997).*
"Extraction and Purification of Plasmid DNA," *Plasmid Vectors*, 1.21-1.45.
Weith et al., "Synthesis of Cellulose Derivatives Containing the Dihydroxyboryl Group and a Study of Their Capacity to Form Specific Complexes with Sugars and Nucleic Acid Components," *Biochemistry*, 9:4396-4401 (1970).
Shih et al., "Chemical Linkage of Nucleic Acids to Neutral and Phosphorylated Cellulose Powders and Isolation of Specific Sequences by Affinity Chromatography," *Biochemistry*, 13:3411-3418 (1974).
Astell et al., "Thermal Elution of Complementary Sequences of Nucleic Acids from Cellulose Columns with Covalently Attached Oligonucleotides of Known Length and Sequence," *J. Biol. Chem.*, 248:1944-1946 (1971).
Kothari et al., "RNA Fractionation on Modified Celluloses," *J. Chromatogr.*, 73:449-462 (1972).
Su et al., "Cellulose as a Matrix for Nucleic Acid Purification," *Analytical Biochemistry*, 267:415-418 (1999).
"Protocol for Genomic DNA Preparation from Fresh or Frozen Serum for PCR Amplification," *BioTechniques*, 29:460-466 (2000).
Ahn et al., "Rapid Mini-Scale Plasmid Isolation for DNA Sequencing and Restriction Mapping," *BioTechniques*, 29:466-468 (2000).
Scott et al., "The use of biomagnetic separation to recover DNA suitable for PCR for Claviceps species," *Letters in Applied Microbiology*, 31:95-99 (2000).
Taylor, et al., "Application for magnetite and silica-magnetite composites to the isolation of genomic DNA," *Journal of Chromatography A*, 890:159-166 (2000).
Levison et al., "Recent developments of magnetic beads for use in nucleic acid purification," *Journal of Chromatography A*, 816:107-111 (1998).
Mrázek et al., "Processing of mRNA from Human Leukocytes By Biomagnetical Separation: Comparison with Current Methods of RNA Isolation," *Acta Univ. Palacki. Olomuc., Fac. Med.*, 142:23-28 (1999).
Davies et al., "Isolation of Plasmid DNA Using Magnetite as a Solid-Phase Adsorbent," *Analytical Biochemistry*, 262:92-94 (1998).
Kotsopoulos et al., "Isolation of 3.5-kb Fragments on Magnetic Solid Supports," *BioTechniques*, 20:198-200 (1996).
Rudi et al., "Rapid, Universal Method to Isolate PCR-Ready DNA Using Magnetic Beads," *BioTechniques*, 22:506-511 (1997).

(Continued)

*Primary Examiner*—Teresa E. Strzelecka
(74) *Attorney, Agent, or Firm*—Townsend and Townsend and Crew LLP

(57) ABSTRACT

A method for the isolation and purification of nucleic acids such as DNA, RNA, and PNA from various sources using cellulose particles or cellulose paper. Adjusting the concentrations of the salt and polyalkylene glycol to the levels that result in binding of nucleic acids to the cellulose particles or cellulose paper. Separating the nucleic acids bound to the cellulose particles or paper and eluting the nucleic acids from the particles or paper.

33 Claims, 1 Drawing Sheet

OTHER PUBLICATIONS

Harris, A.B., "Solvent pH and salt concentration in rapid resolution of nucleic acid bases on cellulose layers," *Biochem. Biophys. Acta*, 145: 520-522 (1967).

Keys et al., "The Use of Cellulose Phosphate in the Extraction of Free Nucleotides from Plant Tissue,"*Proceedings of the Biochemical Society*, pp. 16p-17p.

Nargessi, R.D., U.S. Appl. No. 60/269,729, filed Feb. 16, 2001, entitled: Magnetic Isolation & Purification of Nucleic Acids.

Nargessi, R.D., U.S. Appl. No. 09/972,752, filed Oct. 5, 2001, entitled: Magnetic Isolation & Purification of Nucleic Acids.

Pourfarzaneh et al., "The Use of Magnetizable Particles in Solid Phase Immunoassay," *Methods of Biochemical Analysis*, 1982, vol. 28, pp. 267-295, XP002105006 ISSN: 0076-6941.

Zhang, Yu-ping, et al., "A small-scale procedure for extracting nucleic acids from woody plants infected with various phytopathogens for PCR assay," XP-002259662, *Journal of Virological Methods 71* (1998) pp. 45-50.

\* cited by examiner

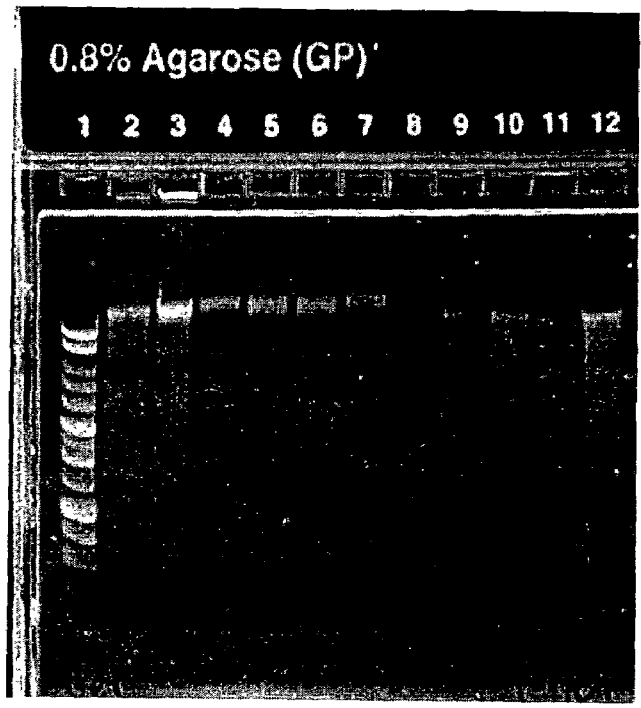

Figure 1. Agarose gel electrophoresis of DNA isolated from whole blood using Cellulose or Qiagen QIAamp DNA Mini Kit. High molecular weight non-degraded DNA is isolated by both techniques.

Lane 1: 1 Kb DNA Ladder
Lane 2: Calf thymus DNA Control
Lane 3: Calf thymus DNA Control processed by Cellulose Particles
Lanes 4, 5, 6, 7 and 8: DNA isolated from blood 4, 5, 8, and 16, using Cellulose Particles (lane 8 is also DNA from blood 16 isolated on a different day)
Lanes 9, 10, 11, and 12: DNA isolated from blood 4, 5, 8, and 16, using QIAamp DNA Mini Kit

ISOLATION AND PURIFICATION OF NUCLEIC ACIDS

CROSS-REFERENCES TO RELATED APPLICATIONS

This application claims the benefit of U.S. Provisional Patent Application Ser. No. 60/337,904, filed Nov. 6, 2001, entitled "ISOLATION AND PURIFICATION OF NUCLEIC ACIDS", the contents of which are hereby incorporated by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK.

Not Applicable

BACKGROUND OF THE INVENTION

Isolation and purification of high quality nucleic acids are critical steps in molecular biology procedures. A number of methods have been reported for the isolation of single and double stranded DNA from biological fluids such as human blood, serum, cultured cells, as well as plants, animal and human tissues, and other specimens. Many different procedures have been described (Taylor, J. I., et al., *J. Chromatography A*, 890:159-166 (2000); Ahn, S. C., et al., *BioTechniques*, 29:466-468 (2000); Scott Jr, D. L. et al., *Lett. Appl. Microl.*, 31:95-99 (2000); Lin, Z. and Floros, J., *BioTechniques*, 29:460-466 (2000); Smith, C. E. and York, C. K., U.S. Pat. No. 6,027,945 (2000); Mrázek, F., and Petrek, M., *Acta Univ. Palacki. Olomuc., Fac. Med.* 142:23-28 (1999); Hawkins, T., U.S. Pat. No. 5,898,071 (1999); Su, X. and Comeau, A., *Anal. Biochem.* 267:415-418 (1999); Hawkins, T., U.S. Pat. No. 5,705,628 (1998); Davies, M. J., et al., *Anal. Biochem.* 262:92-94 (1998); Levison, P. R., et al., *J. Chromatography A*, 816:107-111 (1998); Rudi, K., et al., *BioTechniques*, 22:506-511 (1997); Kotsopoulos, S. K., and Shuber, A. P., *BioTechniques*, 20:198-200 (1996); Boom, W. R., et al., U.S. Pat. No. 5,234,809 (1993); Reeve, M. A., PCT Publication No. WO 91/12079 (1991); Sambrook, J., et al., In: MOLECULAR CLONING, A LABORATORY MANUAL, 2ND EDITION, 1.21-1.45 (1989) Cold Spring Harbor Laboratory Press); Shih, T. Y. and Martin, M. A., *Biochemistry*, 13:3411-3418 (1974); Kothari, R. M. and Taylor, M. W., *J. Chromatogr.*, 73:449-462 (1972); Astell, C. and Smith, M., *J. Biol. Chem.* 246:1944-1946 (1971); Weith, H. L., et. al., *Biochemistry*, 9:4396-4401 (1970). Most of these procedures are time consuming, tedious, and costly. In addition a number of these procedures involve the use of hazardous organic solvents. For example method described by Astell and Smith (1971) requires covalent coupling of oligodeoxyribonucleotides to cellulose. The procedure described by Kothari and Taylor (1972) refers to cellulose and various cellulose derivatives in which one or more organic solvents are used at various stages of nucleic acid isolation and they all require several purification cycles to isolate pure nucleic acids. Moreover, they found that the application of each type of available matrix is often limited to a specific group of nucleic acids.

Su and Comeau (1999) describe isolation of nucleic acid using cellulose and cellulose filter paper. They found that secondary fibril-associated cellulose (designated as SF-cellulose) can be used as a general-purpose matrix to isolate a wide range of nucleic acids. Their procedure, however, involves a complex treatment and conditioning step to prepare the cellulose matrix fibers prior to use for nucleic acid isolation. In addition, prior to the actual purification of nucleic acids, it requires preparation of a crude extract of nucleic acids from the sample into a solution containing detergents or chaotropic salts and removal of the precipitate by centrifugation at >12000×g for 2 min. The complex and lengthy procedure of the method described by Su and Comeau (1999) together with requirement for various organic solvents, make it a laborious and practically impossible technique to automate.

BRIEF SUMMARY OF THE INVENTION

The method described in the present invention, employs polymers having vicinal hydroxyl group(s) such as cellulose particles or cellulose filter paper. Surprisingly, in the presence of certain chemicals and salts, formulated as a binding buffer, these particles or filter paper can adsorb nucleic acids. The nucleic acids bound to the particles or filter paper are then washed, with a wash buffer, to remove any unwanted materials, and the bound nucleic acid is then eluted from the particles or filter paper by adding an elution buffer or deionized water.

The cellulose powder can be purchased for example from Sigma, St. Louis, Mo., or Whatman Inc., Clifton, N.J. The cellulose filter paper can be purchased from Whatman Inc., Clifton, N.J., or Schlecher & Schuell, Keene, N.H.

The binding buffer will generally contain high salt and polyalkylene glycol concentrations. The concentrations of the resulting combination are adjusted to concentrations suitable for binding of nucleic acids to the cellulose. The described binding buffer with slight modifications can also be used as the wash buffer.

The present invention also relates to a method of isolating nucleic acids such as DNA, RNA and PNA, from various sources including biological fluids, tissues, cells, etc. The method comprises binding of nucleic acids, in presence of a binding buffer, to cellulose particles or filter paper, washing the resulting bound nucleic acids with a wash buffer, and eluting the nucleic acids with an elution buffer or deionized water.

The method described herein is also useful for the isolation of both double stranded (ds) or single stranded (ss) polynucleotides (e.g., DNA, RNA, PNA) of virtually any size and from a wide variety of sources.

Still further, the present invention provides a kit comprising cellulose particles or cellulose filter paper and a binding buffer that contains a suitable salt and polyalkylene glycol at concentrations suitable for binding nucleic acids onto cellulose particles or cellulose filter paper. In some embodiments, the kit will also contain a suitable wash buffer, elution buffer, and reagents for lysing cells, tissues or materials from various sources to release the nucleic acids.

BRIEF DESCRIPTION OF THE DRAWINGS

FIG. 1 describes an agarose gel electrophoresis of DNA isolated from whole blood as described in Example 2.

DETAILED DESCRIPTION OF THE INVENTION

General

The present method simplifies the isolation of nucleic acids from various sources by eliminating the need for first purifying the nucleic acids to a semi-purified form, prior to their final purification. In the present method the use of organic solvents including alcohol for extraction or washes is also eliminated. The present method produces nucleic acids immediately ready for further characterization and downstream processing such as PCR, sequencing or blotting procedures. Because of the unique features described herein, the present method is readily adaptable to automation including high throughput screening systems.

Additionally, cellulose particles and cellulose filter paper used in the present invention are commercially available and very inexpensive. The method described herein also avoids the overall lengthy procedure and the need to first prepare a crude preparation of nucleic acids or chemical modification (Su and Comeau (1999)). Still further the present method eliminates the need for chemical modification or chemical coupling or physical adsorption of other materials to cellulose particles or cellulose filter paper, a requirement for procedures described by Astell and Smith (1971) and Kothari and Taylor (1972).

DESCRIPTION OF THE EMBODIMENTS

In the methods below, cellulose particles or cellulose filter paper were found to bind to nucleic acids, in presence of certain concentrations of salt and polyalkylene glycol. Accordingly, the present invention provides in one aspect, a method for simple and rapid isolation of nucleic acids, such as DNA, RNA and PNA, from various sources, including but not limited to body fluids, various solutions, cells, plants, tissues, bacterial cell lysates containing plasmids, etc. Also the invention described is for the isolation of nucleic acids on the basis of size. The following is a description of the present invention with reference to nucleic acids as exemplified by DNA. It is to be understood that the present invention is also useful for separation of RNA and PNA in a similar manner. Because small nucleic acids require higher salt concentrations for strong binding to the cellulose particles (or powder) or cellulose filter paper, salt concentration can be selectively manipulated to release nucleic acids bound to cellulose particles or cellulose filter paper on the basis of size. The cellulose particles or cellulose filter paper having DNA bound thereto can, optionally, be washed with a suitable wash buffer before they are contacted with a suitable elution buffer, to elute and separate the DNA from cellulose particles or cellulose filter paper. Separation of cellulose particles (powder) from the liquid during all the wash and elution steps can be simplified by, for example, placing the cellulose powder in a small column or by using vacuum filtration or centrifugation. Similar procedures can also be used for cellulose filter paper.

In view of the above, the present invention provides in one aspect, a method to bind nucleic acids to cellulose comprising:

a) combining cellulose with a solution containing nucleic acids, thereby producing a combination, and b) adjusting the salt and polyalkylene glycol concentrations of the combination to concentrations suitable for binding the nucleic acids onto the cellulose, whereby all or a portion of the nucleic acids in the solution binds to the cellulose.

One of skill in the art will appreciate that the order of combination of components (e.g., nucleic acids, cellulose, salt and polyalkylene glycol) can be varied so long as the conditions (e.g., concentration of salt and polyalkylene glycol) are sufficient for nucleic acid binding to cellulose. Accordingly, in some embodiments, cellulose will be combined with a solution having a predetermined amount of salt and polyalkyleneglycol that is selected to provide optimum conditions for binding of nucleic acids to the cellulose. This cellulose/salt/polyalkylene glycol combination can then be combined with a mixture containing nucleic acids. The bound nucleic acids can then be purified through washing with an appropriate wash buffer and removed from the cellulose with an elution buffer as described in detail in the Examples.

Alternatively, cellulose can be added directly to a combination containing nucleic acids with salt and polyalkylene glycol at a predetermined concentration which is selected for binding of cellulose to nucleic acids or vice versa.

In any of the methods, the amount of nucleic acids that are bound to the cellulose will typically depend on the amount of cellulose. Preferably, the amount of cellulose is sufficient to avoid saturation of the cellulose particles or cellulose filter paper surface and at least 60%, more preferably 80% and still more preferably 90% or more of the nucleic acids in a solution are bound to the cellulose. In many instances, the portion of nucleic acids bound will be 100%. In some embodiments, however, selective binding of nucleic acids of a particular size can be achieved by manipulation of the salt and polyalkylene glycol concentrations such that only about 5% to about 30% of the total nucleic acid content in a sample is bound to the cellulose.

In the methods of the present invention, the cellulose powder can be purchased for example from Sigma, St. Louis, Mo., or Whatman Inc., Clifton, N.J. The cellulose filter paper can be purchased form Whatman Inc., Clifton, N.J., or Schlecher & Schuell, Keene, N.H.

As described in the present invention, the binding of nucleic acids to the cellulose particles or cellulose filter paper and removal of the non-specifically adsorbed proteins or other substances can be achieved using a solution of salt and polyalkylene glycol at certain concentrations. Useful salts in the present invention are selected from LiCl, $BaCl_2$, $MgCl_2$, CsCl, $CaCl_2$, NaCl, KCl and KI. Preferably the salt is NaCl. Similarly, a variety of polyalkylene glycols are useful in the present invention including, for example, polyethylene glycol and polypropylene glycol. Preferably, the polyalkylene glycol is polyethylene glycol. The salt and polyalkylene reagents are used in concentrations that facilitate binding of nucleic acids to the cellulose particles and cellulose filter paper. Salt concentrations in the binding and wash buffers will depend on the salt being used and milieu from which the nucleic acids are to be isolated and purified. Generally, the salt concentrations will be about 0.25 M to about 5.0 M. More preferably, the salt concentration in the binding and wash buffers is about 0.5 M to about 2.5 M. Still more preferably, the salt concentration is about 0.5 M to about 1.5 M. Most preferably, the salt concentration of the binding buffer is about 1.25 M and the salt concentration of the wash buffer is about 0.5 M. Similarly, the polyalkylene concentration will depend on the polyalkylene used. Polyethylene glycol is commercially available from suppliers such as Sigma Chemical, St. Louis, Mo., USA, and is useful in molecular weights of about 200 to about 10,000, preferably about 1,000 to about 8,000, more preferably about 6,000 to about 8,000. Depending on the weight range of polyethylene glycol used, the concentration can be adjusted.

Generally, for methods in which polyethylene glycol having an average molecular weight of 8,000 is used, the concentration in the binding and wash buffers will be adjusted to about 5% to about 15%, preferably about 10%.

The use of the binding and wash buffers described above, and in the examples below, avoids the use of organic solvents, including ethyl alcohol, commonly used with other nucleic acids isolation procedures.

In the present invention, the cellulose is in the form of particles or powder or filter paper.

In a related aspect, the present invention provides a method of separating nucleic acids from non-nucleic acid materials by binding nucleic acids in a nucleic acid solution to cellulose, comprising:

a) combining cellulose with a solution containing nucleic acids and non-nucleic acid materials to produce a first combination;

b) adjusting the salt and polyethylene glycol concentrations of the first combination to concentrations suitable for binding nucleic acids in the solution to the cellulose, producing a second combination comprising cellulose-bound nucleic acids;

c) separating the cellulose-bound nucleic acids from the second combination;

d) contacting the cellulose-bound nucleic acids separated in c) with an elution buffer to release the bound nucleic acids from the cellulose and into the elution buffer; and e) separating the cellulose from the elution buffer to provide nucleic acids that are substantially free of the non-nucleic acid materials.

In general, the components used in this aspect of the invention are the same as have been described above, and the preferred ranges for salts and polyethylene glycol concentrations are the same as provided above. The elution buffer is preferably a Tris buffer with EDTA. More preferably the elution buffer is about 10 mM Tris, pH 8.0 with about 1 mM EDTA. Also, as noted above, this aspect of the invention can be used with a variety of nucleic acids including, for example, DNA, RNA, PNA or mixtures thereof.

In a particularly preferred embodiment of this aspect of the invention, the nucleic acids bound to cellulose particles or cellulose filter paper are DNA and are washed with a wash buffer, wherein the wash buffer removes impurities bound to the cellulose particles or cellulose filter paper while leaving the DNA bound to the particles or filter paper. More preferably, the DNA bound to the cellulose particles or cellulose filter paper is eluted with an elution buffer that releases the DNA bound to the particles or filter paper, and the DNA is isolated.

In other preferred embodiments, the nucleic acids in solution are a lysate, preferably prepared from cells of human, plant, animal, viral or bacterial origin. Thus, in one application, the cells are from animal, more preferably human. In another application, the cells are from plants. In another application, the cells are of bacterial origin. In still another application, the cells are of viral origin.

The nucleic acids that are separated from non-nucleic acid materials (e.g., peptides, proteins, oligosaccharides, lignans, small molecule natural products and other materials typically of natural origin) are generally obtained in a purity of at least 50%, more preferably at least 80%, still more preferably at least 90% or 95%, and most preferably at least 99% or more.

Accordingly, the present methods are suitable to remove at least 50%, more preferably at least 80%, still more preferably at least 90% or 95%, and most preferably at least 99% or more of the non-nucleic acid materials in a particular sample (e.g., a cell lysate).

In yet another aspect of the invention, polymers and polysaccharides having vicinal hydroxyl groups such as Agarose, Sepharose®, Superdex, Superose, Sephacryl® and Dextran, herein called cellulose derivatives are used. Accordingly, the invention provides a method to bind nucleic acids to cellulose derivatives comprising:

a) combining cellulose derivatives with a solution containing nucleic acids, thereby producing a combination; and b) adjusting the salt and polyalkylene glycol concentrations of the combination to concentrations suitable for binding the nucleic acids onto the cellulose derivatives, whereby all or a portion of the nucleic acids in the solution binds to the cellulose derivatives.

Again, the preferred components and their concentration ranges are essentially the same as provided above. The cellulose derivatives are, in one group of embodiments, selected from polymers having vicinal hydroxyl groups such as Agarose, Sepharose®, Superdex, Superose, Sephacryl® and Dextran and mixtures thereof. Additionally, this method as well as the other methods of the present invention find wide application in the purification of, for example, DNA, RNA, PNA or combinations thereof.

In related methods, the present invention provides a method of separating nucleic acids from non-nucleic acid materials, comprising:

a) combining cellulose derivatives with a solution containing nucleic acids and non-nucleic acid materials to provide a first combination;

b) adjusting the salt and polyethylene glycol concentrations of the first combination to concentrations suitable for binding nucleic acids to the cellulose derivatives, producing a second combination comprising cellulose derivative-bound nucleic acids;

c) separating the cellulose derivative-bound nucleic acids from the second combination;

d) contacting the cellulose derivative-bound nucleic acids separated in c) with an elution buffer to release the bound nucleic acids from the cellulose derivatives and into the elution buffer; and e) separating the cellulose derivatives from the elution buffer to provide nucleic acids that are substantially free of the non-nucleic acid materials.

Preferred embodiments for this aspect of the invention are those that have been described above for the use of cellulose.

Also, as described above, the cellulose derivatives are, in one group of embodiments, selected from polymers containing vicinal hydroxyl groups such as Agarose, Sepharose®, Superdex, Superose, Sephacryl® and Dextran and mixtures thereof.

The present invention will now be illustrated by the following examples, which are not limiting in any way.

EXAMPLES

General Methodology

The cellulose particles used, in the following examples were the cellulose powder from Sigma, St. Louis, Mo. (Catalog Number: C-6288), or Whatman Inc., Clifton, N.J. (Catalog Number: 4021050). The cellulose filter papers (No. 3) were purchased from Whatman Inc., Clifton, N.J. and cut into circular shape with a diameter of approximately 13 millimeters. The Sephadex® G-25 was from Pharmacia, Piscataway, N.J. (Catalog Number: 17-0033-01).

The cellulose particles, cellulose filter papers and Sephadex® were washed with molecular grade deionized water containing 0.02% Sodium Azide prior to use. Cellulose particles and Sephadex® particles were stored in the same buffer at a concentration of 50 mg/ml. Agarose gel electrophoresis was run using E-Gel System (0.8% agarose gels) from Invitrogen, Carlsbad, Calif. The QIAamp DNA Min-Kit from Qiagen, Valencia, Calif., was used as a reference method.

Example 1

DNA Isolation, Using Cellulose Particles

A calf thymus DNA preparation (Sigma, MO, Catalog Number: D1501), used as a control, was reversibly bound to cellulose particles. The DNA bound to cellulose particles was separated and washed from unwanted materials. DNA was then eluted from the particles. The following procedure was used:
1. In a 2 ml microcentifuge tube containing 50 µg (50 µl of a 1 mg/ml DNA solution in STE buffer (100 mM Tris-HCl, pH 8.0, 1 mM EDTA, 500 mM Sodium Chloride)) add 500 µl of the binding buffer (10% PEG 8000 MW, 1.25 M NaCl) and 1 mg (20 µl of a 50 mg/ml suspension) of the cellulose particles.
2. Mix the tube content at room temperature for 10 minutes, using an end-over-end rotator.
3. Sediment the DNA bound to cellulose particles using a microcentrifuge.
4. Wash particles with 1 ml of the wash buffer (10% PEG 8000 MW, 2.5 M NaCl). Repeat the wash step once more.
5. Elute the DNA from particles by adding 200-500 µl of the elution buffer (molecular grade deionized water or TE Buffer (10 mM Tris-HCl, pH 8.0, 1 mM EDTA)), mixing for 10 minutes and sedimenting the particles as described above. The purified DNA is recovered in the supernate and is ready for further analysis.

Results are summarized in Table 1. Total yield of DNA after processing with cellulose particles is >90%, and ≧80% of the input DNA is recovered in the first elution. Additionally, the high 260/280 values (1.8-1.96) indicate the good quality and high purity of the isolated DNA.

Example 2

DNA Isolation from Whole Blood, Using Cellulose Particles

DNA from human whole blood samples was released using Proteinase K and a specially formulated lysis buffer. The DNA was then bound to cellulose particles in presence of the binding buffer. The DNA bound to cellulose particles was then separated and washed from other contaminants. The DNA was eluted from the particles. The following procedure was used:
1. Into a 2 ml microcentrifuge tube, pipet 20 µl (400 µg) of Proteinase K solution in 10 mM Tris-HCl, 1 mM Calcium Chloride, 50% Glycerol, pH 7.5.
2. Add 200 µl of whole blood (Heparin-, Citrate- or EDTA-treated).
3. Add 200 µl of the lysis buffer (50 mM Tris-HCl, 50 mM EDTA, 6 M Guanidine-HCl, 6 M Urea, 10 mM Calcium Chloride, 10% Tween-20).
4. Mix the tube content by pulse-vortexing for 15 sec.
5. Incubate the tube content at 56° C. for 10 minutes.
6. Remove the tube from 56° C., and added 500 µl of the binding buffer (10% PEG 8000 MW, 1.25 M NaCl), followed by 20 µl (1 mg) of the well-mixed cellulose particles suspension.
7. Incubate the tube content for 10 min at room temperature, while mixing on an end-over-end rotator.
8. Sediment the cellulose particles-bound DNA using a microcentrifuge.
9. Aspirate the supernate and wash the particles by adding 1 ml of the wash buffer (10% PEG 8000 MW, 2.5 M NaCl), mixing well and aspirating the supernate. Repeat the wash step once more.
10. Add 200-500 µl of the elution buffer (10 mM Tris-HCl, pH 8.0, 1 mM EDTA) or molecular grade deionized water, and mix as in step 7, above.
11. Sediment the particles using a microcentrifuge and carefully collect the supernate containing the purified DNA.
12. The purified DNA is then ready for further analysis.

Agarose gel electorphoresis of the DNA isolated from whole blood samples by the method of present invention showed a single non-degraded high molecular weight DNA band (FIG. 1).

Example 3

DNA Isoaltion, Using Cellulose Filter Paper in a Microtube

One circular layer of Whatman Filter Paper was used as a matrix for capturing DNA in a specially formulated binding buffer. The captured DNA was washed with a wash buffer to remove unwanted materials and the purified DNA was then eluted from the filter paper. The following procedure was used:
1. Cut one uniform circular layer (13 mm diameter) of the cellulose filter paper and place it into a 2 ml microcentrifuge tube.
2. Wash the filter paper first with 2 ml of molecular grade deionized water, followed by 2 ml of the binding buffer (10% PEG 8000 MW, 1.25 M NaCl).
3. Add 500 µl of the binding buffer into the tube followed by 50 µl of a 1 mg/ml calf thymus DNA solution in STE Buffer (100 mM Tris-HCl, pH 8.0, 1 mM EDTA, 500 mM NaCl).
4. Incubate the tube at room temperature for 10 minutes while mixing on an end-over-end rotator.
5. Aspirate the solution (liquid) from the microtube containing the filter paper and wash the filter paper twice, each time with 1 ml of the wash buffer (10% PEG 8000 MW, 2.5 M NaCl).
6. Add 200-500 µl of the elution buffer (10 mM Tris-HCl, pH 8.0, 1 mM EDTA) or molecular grade deionized water. Mix for 10 minutes as in Step 4, above.
7. Carefully transfer the purified DNA (in the elution buffer) from the microtube containing the filter paper into a clean tube. The DNA is ready for further processing.

Results are shown in Table 2. Approximately 25% of the input DNA was recovered under the conditions used. As shown in Example 4 below, increasing the number of filter paper layers would increase the DNA recovery.

Example 4

DNA Isoation, Using Cellulose Filter Paper(s) in a Column

One or three circular layers of cellulose filter paper were used as a matrix in a column for capturing DNA in a specially formulated binding buffer. The captured DNA was washed with a wash buffer to remove unwanted materials and the purified DNA was then eluted from the column. The following procedure was used:
1. Cut uniform circle layers of the filter paper as in example 3 above, and place 1 or 3 layers at the bottom of a column (0.5×10 cm).
2. Wash the filter paper(s) in the column with 2 ml of molecular grade deionized water, followed by 2 ml of the binding buffer (10% PEG 8000 MW, 1.25 M NaCl). For each wash, simply allow the liquid to drain from the column by gravity.
3. Add 500 µl of the binding buffer into the column followed by 50 µl of a 1 mg/ml calf thymus DNA solution in STE Buffer (100 mM Tris-HCl, pH 8.0, 1 mM EDTA, 500 mM NaCl).
4. Allow the liquid to drain from the column by gravity.
5. Wash the filter papers in the column twice each with 500 µl of the wash buffer (10% PEG 8000 MW, 2.5 M NaCl).
6. Add 200-500 µl of the elution buffer (10 mM Tris-HCl, pH 8.0, 1 mM EDTA) or molecular grade deionized water. Collect the purified DNA, which is ready for further analysis.

Results are shown in Table 2. Using 1 layer of filter paper ~75% of the input DNA was recovered. Increasing the number of layers to 3 increased the DNA recovery to 100%.

Note: A vacuum pump can be used to facilitate the washing step.

Example 5

Isolation of DNA, Using Sephadex® G-25 in a Microtube

Sephadex® G-25 was used as a matrix for capturing DNA in a specially formulated binding buffer. The captured DNA was washed with a wash buffer to remove unwanted materials and the purified DNA was then eluted from the column. The following procedure was used:
1. Prepare a 50 mg/ml suspension of Sephadex® G-25 in molecular grade water containing 0.02% Sodium Azide.
2. Pipet 1 mg (20 µl), 5 mg (100 µl) and 10 mg (200 µl) of the Sephadex® G-25 suspension into three individual microcentrifuge tubes.
3. Add 500 µl of the binding buffer (10% PEG, MW 8000, 1.25 M NaCl).
4. Add 50 µl of a 1 mg/ml calf thymus DNA solution in STE Buffer (100 mM Tris-HCl, pH 8.0, 1 mM EDTA, 500 mM NaCl).
5. Incubate for 10 minutes at room temperature, while mixing on an end-over-end rotator.
6. Wash the Sephadex® particles twice, each with 1 ml of the wash buffer (10% PEG, MW 8000, 2.5 M NaCl). Use a microcentrifuge to sediment the particles and aspirate the supernate.
7. Add 200-500 µl of the elution buffer (10 mM Tris-HCl, pH 8.0, 1 mM EDTA) or molecular grade deionized water.
8. Incubate for 10 minutes at room temperature as in Step 5, above.
9. Sediment the particles using a microcentrifuge.
10. Carefully transfer the supernate containing the purified DNA into a clean microtube. The DNA is ready for further analysis.

Results shown in Table 3 are comparable with those obtained with cellulose particles under the same conditions.

Example 6

Isolation of DNA, Using Sephadex® G-25 in a Column

Sephadex® G-25 packed in a column was used as a matrix for capturing DNA in a specially formulated binding buffer. The captured DNA was washed with a wash buffer to remove unwanted materials and the purified DNA was then eluted from the column. The following procedure was used:
1. Prepare a 50 mg/ml suspension of Sephadex® G-25 in molecular grade water containing 0.02% Sodium Azide.
2. Pack 2 individual columns (0.5×10 cm) with 1 mg (20 µl) or 5 mg (100 µl) of the Sephadex® G-25 suspension.
3. Add 500 µl of the binding buffer (10% PEG, MW 8000, 1.25 M NaCl).
4. Add 50 µl of a 1 mg/ml calf thymus DNA solution in STE Buffer (100 mM Tris-HCl, pH 8.0, 1 mM EDTA, 500 mM NaCl).
5. Incubate for 10 minutes at room temperature.
6. Allow the liquid to drain from the column by gravity.
7. Wash the Sephadex® particles in the column twice, each time with 1 ml of the wash buffer (10% PEG, MW 8000, 2.5 M NaCl).
8. Add 200-500 µl of the elution buffer (10 mM Tris-HCl, pH 8.0, 1 mM EDTA) or molecular grade deionized water.
9. Collect the purified DNA into a clean tube.
10 The DNA is ready for further analysis.

Results shown in Table 4 indicate that increasing the amount of Sephadex® G-25 in the column increases the yield of DNA.

TABLE 1

Recovery of Calf Thymus DNA from Cellulose Particles

| Elution and Run # | DNA (µg) | 260/280 | % Recovery |
|---|---|---|---|
| 1st Elution, Run #1 | 41.70 | 1.87 | 83.40 |
| 2nd Elution, Run #1 | 5.44 | 1.96 | 10.88 |
| 1st Elution, Run #2 | 39.40 | 1.85 | 78.80 |
| 2nd Elution, Run #2 | 9.12 | 1.80 | 18.24 |

TABLE 2

Recovery of Calf Thymus DNA from Filter Paper
(1 Layer in Microtube vs. 1 or 3 Layers in Column)

| System | DNA (µg) | | 260/280 |
|---|---|---|---|
| 1 Layer Filter Paper in Microtube | 10.48 | Elution 1 | 1.88 |
| | 1.94 | Elution 2 | 1.91 |
| 1 Layer Filter Paper in Column | 11.01 | Elution 1 | 1.86 |
| | 11.41 | Elution 2 | 1.87 |
| | 7.19 | Elution 3 | 1.87 |
| | 5.50 | Elution 4 | 1.87 |
| | 2.37 | Elution 5 | 1.89 |
| 3 Layers Filter Papers in Column | 1.06 | Elution 1 | 1.76 |
| | 2.41 | Elution 2 | 1.89 |
| | 3.25 | Elution 3 | 1.88 |
| | 5.57 | Elution 4 | 1.86 |
| | 5.69 | Elution 5 | 1.86 |
| | 7.46 | Elution 6 | 1.85 |

TABLE 2-continued

Recovery of Calf Thymus DNA from Filter Paper
(1 Layer in Microtube vs. 1 or 3 Layers in Column)

| System | DNA (μg) | 260/280 |
|---|---|---|
| | 18.98 Elution 7 | 1.87 |
| | 5.03 Elution 8 | 1.88 |
| | 1.69 Elution 9 | 1.95 |

TABLE 3

Recovery of Calf Thymus DNA from Sephadex ® G-25 Vs. Cellulose Particles

| Volume/Tube | Sephadex ® DNA (μg) | Sephadex ® 260/280 | Cellulose DNA (μg) | Cellulose 260/280 |
|---|---|---|---|---|
| 20 μl | 21.24 Elution 1 | 1.86 | 22.68 Elution 1 | 1.86 |
| | 27.0 Elution 2 | 1.82 | 26.27 Elution 2 | 1.83 |
| 100 μl | 19.67 Elution 1 | 1.87 | 25.79 Elution 1 | 1.86 |
| | 19.33 Elution 2 | 1.86 | 24.53 Elution 2 | 1.86 |
| 200 μl | 16.40 Elution 1 | 1.86 | 24.67 Elution 1 | 1.86 |
| | 8.62 Elution 2 | 1.86 | 24.50 Elution 2 | 1.84 |

TABLE 4

Recovery of Calf Thymus DNA from Sephadex ® G-25 Packed in a Column

| Volume/column | DNA (μg) | 260/280 |
|---|---|---|
| 20 μl | 11.48 Elution 1 | 1.85 |
| | 6.58 Elution 2 | 1.87 |
| 100 μl | 17.13 Elution 1 | 1.64 |
| | 9.10 Elution 2 | 1.86 |

What is claimed is:

1. A method to bind nucleic acids to cellulose, wherein said nucleic acids have not been purified or semi-purified, said method comprising:
   a) combining cellulose, wherein said cellulose is not chemically coupled or physically adsorbed to another material, with a solution containing said nucleic acids, thereby producing a combination, and
   b) adjusting the salt and polyalkylene glycol concentrations of the combination to final concentrations suitable for binding the nucleic acids to the cellulose using a binding buffer having a concentration of from 0.5 M to 1.5 M salt and from 5% to 15% polyalkylene glycol, whereby all or a portion of the nucleic acids in the solution binds to the cellulose, and wherein the nucleic acids bind to the cellulose while the nucleic acids are in a non-aggregated state.

2. The method of claim 1, wherein the nucleic acids are DNA and the polyalkylene glycol is polyethylene glycol.

3. The method of claim 2, wherein the polyethylene glycol has a molecular weight of from about 1000 to about 8000, and wherein the salt is sodium chloride.

4. The method of claim 2, wherein the polyethylene glycol has a molecular weight of from about 6000 to about 8000, and wherein the salt is sodium chloride.

5. The method of claim 1, wherein the nucleic acids are RNA and the polyalkylene glycol is polyethylene glycol.

6. The method of claim 1, wherein the cellulose is in the form of particles.

7. A method of separating nucleic acids from non-nucleic acid materials in a nucleic acid solution, wherein said nucleic acids have not been purified, said method comprising:
   a) combining cellulose particles with a solution containing said nucleic acids and non-nucleic acid materials to produce a first combination;
   b) adjusting the salt and polyethylene glycol concentrations of the first combination to concentrations suitable for binding said nucleic acids in the solution to the cellulose particles using a binding buffer having a concentration of from 0.5 M to 1.5 M salt and from 5% to 15% polyethylene glycol, producing a second combination comprising cellulose-bound nucleic acids, and wherein the nucleic acids bind to the cellulose while the nucleic acids are in a non-aggregated state;
   c) separating the cellulose-bound nucleic acids from the second combination;
   d) contacting the cellulose-bound nucleic acids separated in c) with an elution buffer to release the bound nucleic acids from the cellulose particles and into the elution buffer; and
   e) separating the cellulose particles from the elution buffer to provide nucleic acids that are substantially free of the non-nucleic acid materials, wherein the separation of the cellulose particles in step c) and e) is carried out using a centrifuge or a column.

8. The method of claim 7, wherein the separation of the cellulose particles in step c) and e) is carried out using a centrifuge.

9. The method of claim 7, wherein the separation of the cellulose particles in step c) and e) is carried out using a column.

10. The method of claim 7, wherein the nucleic acids bound to cellulose particles are DNA and are washed with a wash buffer, wherein the wash buffer removes impurities bound to the cellulose particles while leaving the DNA bound to the cellulose particles.

11. The method of claim 10, wherein the DNA bound to the cellulose particles is eluted with an elution buffer that releases the DNA bound to the cellulose particles.

12. The method of claim 11, wherein the DNA released by the elution buffer is isolated.

13. The method of claim 7, wherein the polyethylene glycol has a molecular weight of about 1000 to about 8000, and wherein the salt is sodium chloride.

14. The method of claim 7, wherein the polyethylene glycol has a molecular weight of about 6000 to about 8000, and wherein the salt is sodium chloride.

15. The method of claim 7, wherein the nucleic acids and non-nucleic acid materials are obtained from a cell lysate.

16. The method of claim 15, wherein the lysate is prepared from cells of human, animal, plant, viral or bacterial origin.

17. A method to bind nucleic acids to cellulose paper, wherein said nucleic acids have not been purified or semi-purified, said method comprising:
   a) combining cellulose paper with a solution containing said nucleic acids, thereby producing a combination, and
   b) adjusting the salt and polyalkylene glycol concentrations of the combination to concentrations suitable for binding the nucleic acids to the cellulose paper using a binding buffer having a concentration of from 0.5 M to 1.5 M salt and from 5% to 15% polyalkylene glycol, whereby all or a portion of the nucleic acids in the solution binds to the cellulose paper, and wherein the nucleic acids bind to the cellulose while the nucleic acids are in a non-aggregated state.

18. The method of claim 17, wherein the cellulose paper is from the group consisting of various thickness and combinations thereof.

19. The method of claim 17, wherein the nucleic acids are DNA and the polyakylene glycol is polyethylene glycol.

20. The method of claim 17, wherein the nucleic acids are RNA and the polyakylene glycol is polyethylene glycol.

21. The method of claim 19, wherein the polyethylene glycol has an average molecular weight of from about 1000 to about 8000, and wherein the salt is sodium chloride.

22. The method of claim 19, wherein the polyethylene glycol has an average molecular weight of from about 6000 to about 8000, and wherein the salt is sodium chloride.

23. A method of separating nucleic acids from non-nucleic acid materials, wherein said nucleic acids have not been purified or semi-purified, said method comprising:
   a) combining cellulose paper with a solution containing said nucleic acids and non-nucleic acid materials to provide a first combination;
   b) adjusting the salt and polyethylene glycol concentrations of the first combination to concentrations suitable for binding said nucleic acids to the cellulose paper using a binding buffer having a concentration of from 0.5 M to 1.5 M salt and from 5% to 15% polyethylene glycol, producing a second combination comprising cellulose paper-bound nucleic acids, and wherein the nucleic acids bind to the cellulose while the nucleic acids are in a non-aggregated state;
   c) separating the cellulose paper-bound nucleic acids from the second combination;
   d) contacting the cellulose paper-bound nucleic acids separated in c) with an elution buffer to release the bound nucleic acids from the cellulose paper and into the elution buffer; and
   e) separating the cellulose paper from the elution buffer to provide nucleic acids that are substantially free of the non-nucleic acid materials.

24. The method of claim 23, wherein the separation of the cellulose paper in steps c) and e) is carried out manually or by centrifugation.

25. The method of claim 23, wherein the separation of the cellulose paper in steps c) and e) is carried out by placing it in a column.

26. The method of claim 23, wherein the nucleic acids bound to cellulose paper are washed with a wash buffer, wherein the wash buffer removes impurities bound to the cellulose paper while leaving the nucleic acids bound to the cellulose paper.

27. The method of claim 26, wherein the nucleic acids bound to the cellulose paper are DNA and are eluted with an elution buffer, wherein the elution buffer releases the DNA bound to the cellulose paper.

28. The method of claim 27, wherein the DNA released by the elution buffer is isolated.

29. The method of claim 23, wherein the polyethylene glycol has an average molecular weight of about 1000 to about 8000, and wherein the salt is sodium chloride.

30. The method of claim 23, wherein the polyethylene glycol has an average molecular weight of about 6000 to about 8000, and wherein the salt is sodium chloride.

31. The method of claim 23, wherein the nucleic acids and non-nucleic acid materials are obtained from a cell lysate.

32. The method of claim 31, wherein the lysate is prepared from cells of human, animal, plant, viral or bacterial origin.

33. A method for binding nucleic acids to cellulose, comprising combining cellulose, wherein said cellulose is not chemically coupled or physically adsorbed to another material, with nucleic acids that have not been purified or semi-purified in a mixture containing sodium chloride at a concentration of from about 0.7 M to 2.5 M and a polyethylene glycol at a concentration of from about 5% to 10%, said concentrations being sufficient to bind said nucleic acids to said cellulose while the nucleic acids are in a non-aggregated state.

* * * * *